United States Patent
Kauphusman et al.

(10) Patent No.: US 10,285,753 B2
(45) Date of Patent: May 14, 2019

(54) CIRCUIT FOR A CATHETER OR SHEATH AND METHOD OF FORMING SAME

(71) Applicant: St. Jude Medical, Atrial Fibrillation Division, Inc., St. Paul, MN (US)

(72) Inventors: James V. Kauphusman, Champlin, MN (US); Allan M. Fuentes, Spring Hill, FL (US); Troy T. Tegg, Elk River, MN (US); Dale E. Just, Minneapolis, MN (US)

(73) Assignee: ST. JUDE MEDICAL, ATRIAL FIBRILLATION DIVISION, INC., St. Paul, MN (US)

( * ) Notice: Subject to any disclaimer, the term of this patent is extended or adjusted under 35 U.S.C. 154(b) by 395 days.

(21) Appl. No.: 14/599,852

(22) Filed: Jan. 19, 2015

(65) Prior Publication Data

US 2015/0196356 A1   Jul. 16, 2015

Related U.S. Application Data

(63) Continuation of application No. 12/443,417, filed as application No. PCT/US2007/080945 on Oct. 10, 2007, now Pat. No. 8,968,299.

(Continued)

(51) Int. Cl.
*A61B 18/14* (2006.01)
*A61B 5/042* (2006.01)
(Continued)

(52) U.S. Cl.
CPC .......... *A61B 18/1492* (2013.01); *A61B 5/042* (2013.01); *A61B 5/0422* (2013.01);
(Continued)

(58) Field of Classification Search
CPC ...... A61B 18/1492; A61B 2018/00577; A61B 2018/0016; A61B 2018/00351;
(Continued)

(56) References Cited

U.S. PATENT DOCUMENTS

| | | |
|---|---|---|
| 4,890,623 A | 1/1990 | Cook |
| 5,080,660 A | 1/1992 | Buelna |

(Continued)

FOREIGN PATENT DOCUMENTS

WO   2005032362   4/2005

OTHER PUBLICATIONS

Carson, et al. "Improved Circuit Flexibility Using Laser Thinning". Jan. 1999. Motorola, Inc. p. 12 (Year: 1999).*

(Continued)

*Primary Examiner* — Nathan R Price
*Assistant Examiner* — Weng Lee
(74) *Attorney, Agent, or Firm* — Dykema Gossett PLLC (57) ABSTRACT

A circuit configured for connecting an electrode to a catheter or sheath is disclosed. The circuit includes a member having a longitudinal axis and configured to extend along at least a portion of the length of the catheter or sheath. The circuit further includes a trace printed on the member, where the trace includes at least a longitudinal segment extending generally along at least a portion of the longitudinal axis and a transverse segment extending generally transverse to the longitudinal axis. In an embodiment, the circuit further includes a pad integral with and extending from the circuit proximal the transverse segment of the trace. A catheter or sheath assembly comprising the circuit and an electrode connected to the circuit is also disclosed. A method of forming a catheter or sheath assembly is also provided.

18 Claims, 4 Drawing Sheets

Related U.S. Application Data (60) Provisional application No. 60/828,939, filed on Oct. 10, 2006.

(51) Int. Cl.
| | | |
|---|---|---|
| *A61B 5/00* | (2006.01) | |
| *A61M 25/01* | (2006.01) | |
| *A61B 18/18* | (2006.01) | |
| *A61B 18/00* | (2006.01) | |
| *A61N 7/02* | (2006.01) | |
| *A61B 17/00* | (2006.01) | |

(52) U.S. Cl.
CPC ....... *A61B 5/6852* (2013.01); *A61M 25/0147* (2013.01); *A61B 18/18* (2013.01); *A61B 18/1815* (2013.01); *A61B 2017/00323* (2013.01); *A61B 2018/0016* (2013.01); *A61B 2018/00023* (2013.01); *A61B 2018/00029* (2013.01); *A61B 2018/00214* (2013.01); *A61B 2018/00244* (2013.01); *A61B 2018/00285* (2013.01); *A61B 2018/00351* (2013.01); *A61B 2018/00577* (2013.01); *A61B 2018/00654* (2013.01); *A61B 2018/00839* (2013.01); *A61B 2018/00898* (2013.01); *A61B 2018/00994* (2013.01); *A61B 2018/1467* (2013.01); *A61B 2018/1497* (2013.01); *A61B 2018/1861* (2013.01); *A61B 2560/066* (2013.01); *A61B 2562/222* (2013.01); *A61N 7/02* (2013.01); *Y10T 29/4913* (2015.01)

(58) Field of Classification Search
CPC .... A61B 2018/1497; A61B 2018/1467; A61B 5/0422; A61M 25/0147; A61M 2025/0166
See application file for complete search history.

(56) References Cited

U.S. PATENT DOCUMENTS

| | | | | |
|---|---|---|---|---|
| 5,313,943 | A | * | 5/1994 | Houser ................ A61B 5/0422 600/374 |
| 5,318,525 | A | | 6/1994 | West |
| 5,348,554 | A | | 9/1994 | Imran |
| 5,403,311 | A | | 4/1995 | Abele et al. |
| 5,456,682 | A | | 10/1995 | Edwards et al. |
| 5,476,495 | A | | 12/1995 | Kordis |
| 5,571,085 | A | | 11/1996 | Accisano |
| 5,681,282 | A | | 10/1997 | Eggers et al. |
| 5,683,366 | A | | 11/1997 | Eggers et al. |
| 5,728,094 | A | | 3/1998 | Edwards |
| 5,755,766 | A | | 5/1998 | Chastain |
| 5,766,153 | A | | 6/1998 | Eggers |
| 5,785,705 | A | | 7/1998 | Baker |
| 5,797,903 | A | | 8/1998 | Swanson et al. |
| 5,843,152 | A | | 12/1998 | Tu |
| 5,885,238 | A | | 3/1999 | Stevens et al. |
| 5,954,665 | A | | 9/1999 | Ben-Haim |
| 6,015,407 | A | | 1/2000 | Rieb et al. |
| 6,068,629 | A | * | 5/2000 | Haissaguerre ......... A61B 18/08 600/374 |
| 6,117,088 | A | | 9/2000 | Kreizman |
| 6,168,593 | B1 | | 1/2001 | Sharkey |
| 6,210,406 | B1 | | 4/2001 | Webster |
| 6,226,554 | B1 | | 5/2001 | Tu et al. |
| 6,277,107 | B1 | | 8/2001 | Lurie |
| 6,394,956 | B1 | | 5/2002 | Chandrasekaran |
| 6,494,880 | B1 | | 12/2002 | Swanson |
| 6,517,477 | B1 | | 2/2003 | Wendlandt |
| 6,544,215 | B1 | | 4/2003 | Bencini et al. |
| 6,554,794 | B1 | | 4/2003 | Mueller |
| 6,602,242 | B1 | | 8/2003 | Fung |
| 6,726,677 | B1 | | 4/2004 | Flaherty |
| 6,743,239 | B1 | | 6/2004 | Kuehn |
| 6,945,956 | B2 | | 9/2005 | Waldhauser |
| 7,717,899 | B2 | | 5/2010 | Bowe et al. |
| 2001/0007070 | A1 | | 7/2001 | Stewart |
| 2002/0029030 | A1 | | 3/2002 | Lurie |
| 2002/0111618 | A1 | | 8/2002 | Stewart |
| 2002/0128639 | A1 | | 9/2002 | Pless |
| 2002/0165537 | A1 | | 11/2002 | Kelley |
| 2003/0050637 | A1 | | 3/2003 | Maguire et al. |
| 2003/0114832 | A1 | | 6/2003 | Kohler |
| 2003/0130712 | A1 | * | 7/2003 | Smits ................ A61M 25/0138 607/116 |
| 2003/0181900 | A1 | | 9/2003 | Long |
| 2003/0212394 | A1 | * | 11/2003 | Pearson ............. A61B 18/1477 606/41 |
| 2004/0010303 | A1 | * | 1/2004 | Bolea .................. A61B 5/02028 607/118 |
| 2004/0030331 | A1 | | 2/2004 | Thomas et al. |
| 2004/0143256 | A1 | | 7/2004 | Bednarek |
| 2005/0065508 | A1 | * | 3/2005 | Johnson ............... A61B 5/0422 606/41 |
| 2005/0159799 | A1 | | 7/2005 | Daglow |
| 2005/0234436 | A1 | | 10/2005 | Baxter |
| 2005/0272975 | A1 | | 12/2005 | McWeeney |
| 2006/0100618 | A1 | * | 5/2006 | Chan .................. A61B 18/1492 606/41 |
| 2007/0179486 | A1 | | 8/2007 | Welch |
| 2010/0094279 | A1 | | 4/2010 | Kauphusman |
| 2012/0029334 | A1 | | 2/2012 | Tegg |

OTHER PUBLICATIONS

Author:, Dherve, Gwenaelle, Title: Supplementary European Search Report, Citation: EP 07 84 4086, dated Jun. 6, 2011, 3 pgs.
Author:, Dherve, Gwenaelle, Title: Supplementary European Search Report, Citation: EP 07844081, dated Jun. 15, 2011, 3 pgs.
Author: Hammill, Stephen C., Title: Epicardial Ablation: Reducing the Risks, Citation: Cardiovasc Electrophysiol, vol. 17, Reference pp. 550-552, Publication Date: May 2006.
Author: Schweikert, Robert A., Title: Percutaneous Pericardial Instrumentation for Endo-Epicardial Mapping of Previously Failed Ablations, Citation: Circulation 2003; 108, Reference pp. 1329-1335, Publication Date: Sep. 2, 2003.
A International Search Report for PCT Application No. PCT/US2007/080929, dated Jun. 23, 2008. 3 pgs.
A International Search Report for PCT Application No. PCT/US07/80945, dated Apr. 3, 2008, 3 pgs.
A International Search Report for PCT Application No. PCT/US07/80939, dated Jul. 25, 2008. 3 pgs.
A International Search Report for PCT Application No. PCT/US2007/080817, dated Apr. 24, 2008. 3 pgs.
A Extended European Search Report for EP Application No. 15159972, dated Jul. 1, 2015. 3 pgs.

* cited by examiner

CIRCUIT FOR A CATHETER OR SHEATH AND METHOD OF FORMING SAME

CROSS-REFERENCE TO RELATED APPLICATIONS

This application is a continuation of U.S. application Ser. No. 12/443,417, filed 27 Mar. 2009 (the '417 application), now pending, which is a national stage application of international application no. PCT/US2007/080945, filed 10 Oct. 2007 (the '945 application), which in turn claims the benefit of U.S. application No. 60/828,939, filed 10 Oct. 2006 (the '939 application), now expired. The '417 application, '945 application and '939 application are each hereby incorporated by reference as though fully set forth herein.

BACKGROUND OF THE INVENTION a. Field of the Invention

The instant invention relates to a circuit for a catheter or sheath, including a circuit with a trace printed on the circuit and configured for connection to an electrode.

b. Background Art

Catheters have been in use for medical procedures for many years. Catheters can be used for medical procedures to examine, diagnose, and treat while positioned at a specific location within a body that is otherwise inaccessible without more invasive procedures. During these procedures a catheter is commonly inserted into a vessel near the surface of the body and is guided to a specific location within the body for examination, diagnosis, and/or treatment. For example, one procedure often referred to as "catheter ablation" utilizes a catheter to convey an electrical stimulus to a selected location within the human body to create tissue necrosis. Another procedure often referred to as "mapping" utilizes a catheter with sensing electrodes to monitor various forms of electrical activity in the human body.

Catheters are also used increasingly for medical procedures involving the human heart. Typically, the catheter is inserted in an artery or vein in the leg, neck, or arm of the patient and directed, sometimes with the aid of a guide wire or introducer, through the vessels until a distal tip of the catheter reaches the desired location for the medical procedure in the heart.

A typical human heart includes a right ventricle, a right atrium, a left ventricle, and a left atrium. The right atrium is in fluid communication with the superior vena cava and the inferior vena cava. The atrioventricular septum separates the right atrium from the right ventricle. The tricuspid valve contained within the atrioventricular septum provides communication between the right atrium and the right ventricle.

In a normal heart, contraction and relaxation of the heart muscle (myocardium) takes place in an organized fashion as electro-chemical signals pass sequentially through the myocardium from the sinoatrial (SA) node, which comprises a bundle of unique cells disposed in the wall of the right atrium, to the atrioventricular (AV) node and then along a well-defined route, which includes the His-Purkinje system, into the left and right ventricles. The AV node lies near the ostium of the coronary sinus in the interatrial septum in the right atrium. Each cell membrane of the SA node has a characteristic tendency to leak sodium ions gradually over time such that the cell membrane periodically breaks down and allows an inflow of sodium ions, thereby causing the SA node cells to depolarize. The SA node cells are in communication with the surrounding atrial muscle cells such that the depolarization of the SA node cells causes the adjacent atrial muscle cells to depolarize. This results in atrial systole, wherein the atria contract to empty and fill blood into the ventricles. The atrial depolarization from the SA node is detected by the AV node which, in turn, communicates the depolarization impulse into the ventricles via the bundle of His and Purkinje fibers following a brief conduction delay. The His-Purkinje system begins at the AV node and follows along the membranous interatrial septum toward the tricuspid valve through the atrioventricular septum and into the membranous interventricular septum. At about the middle of the interventricular septum, the His-Purkinje system splits into right and left branches which straddle the summit of the muscular part of the interventricular septum.

Sometimes abnormal rhythms occur in the heart, which are referred to generally as arrhythmia. For example, a common arrhythmia is Wolff-Parkinson-White syndrome (W-P-W). The cause of W-P-W is generally believed to be the existence of an anomalous conduction pathway or pathways that connect the atrial muscle tissue directly to the ventricular muscle tissue, thus bypassing the normal His-Purkinje system. These pathways are usually located in the fibrous tissue that connects the atrium and the ventricle. Another arrhythmia is ventricular tachycardia ("V.T."). VT is a disease of the ventricles of the heart in which the heart's normal arrhythmic contraction is altered. Frequently, the rate of heart beat is too fast, although the conditions of the disease itself are generally quite complex. VT may occur most often in patients following a myocardial infarction. A myocardial infarction, commonly referred to as a heart attack, is a loss of blood to a region of the heart causing the myocardial tissue in that region to die and be replaced by an area of scar tissue known as a myocardial infarct. Frequently, the myocardial infarct is present in the left ventricle. As a result of the myocardial infarct, circular pathways ("reentry circuits") are frequently created within the left ventricle which conduct electrical impulses of the heart. These reentry circuits may cause the electrical impulses of the heart to travel in circles about the myocardial infarct, frequently causing an erratic and sometimes accelerated beating of the heart. These reentry circuits may also occur around discrete elements of the heart, such as valves. In addition, the reentry circuits sometime occur around both the myocardial infarct and the discrete elements of the heart.

Other abnormal arrhythmias sometimes occur in the atria, which are referred to as atrial arrhythmia. Three of the most common atrial arrhythmia are ectopic atrial tachycardia, atrial fibrillation, and atrial flutter. Atrial fibrillation can result in significant patient discomfort and even death because of a number of associated problems, including the following: an irregular heart rate, which causes patient discomfort and anxiety; loss of synchronous atrioventricular contractions, which compromises cardiac hemodynamics, resulting in varying levels of congestive heart failure; and stasis of blood flow, which increases the likelihood of thromboembolism.

Efforts to alleviate these problems in the past have included significant usage of pharmacological treatments. While pharmacological treatments are sometimes effective, in some circumstances drug therapy has had only limited effectiveness and is frequently plagued with side effects, such as dizziness, nausea, vision problems, and other difficulties.

An increasingly common medical procedure for the treatment of certain types of cardiac arrhythmia and atrial arrhythmia involves the ablation of tissue in the heart to cut off the path for stray or improper electrical signals. Such procedures are performed many times with an ablation catheter. Typically, the ablation catheter is inserted in an artery or vein in the leg, neck, or arm of the patient and threaded, sometimes with the aid of a guidewire or introducer, through the vessels until a distal tip of the ablation catheter reaches the desired location for the ablation procedure in the heart (endocardial ablation). Ablation may also be performed from outside the heart (epicardial ablation) using devices introduced into the chest. The ablation catheters commonly used to perform these ablation procedures produce lesions and electrically isolate or render the tissue non-contractile at particular points in the cardiac tissue by physical contact of the cardiac tissue with an electrode of the ablation catheter and application of energy. The lesion partially or completely blocks the stray electrical signals to lessen or eliminate arrhythmia.

Another medical procedure using ablation catheters with sheaths to ablate accessory pathways associated with W-P-W utilizing both a transseptal and retrograde approach is discussed in Saul, J. P., et al., "Catheter Ablation of Accessory Atrioventricular Pathways in Young Patients: Use of long vascular sheaths, the transseptal approach and a retrograde left posterior parallel approach," Journal of the American College of Cardiology, Vol. 21, no. 3, pgs. 571 583 (1 Mar. 1993). Other catheter ablation procedures are disclosed in Swartz, J. F., "Radiofrequency Endocardial Catheter Ablation of Accessory Atrioventricular Pathway Atrial Insertion Sites," Circulation, Vol. 87, no. 2, pgs. 487 499 (February 1993).

Ablation of a specific location within or near the heart typically requires the precise placement of the ablation catheter. Precise positioning of the ablation catheter is especially difficult because of the physiology of the heart, particularly because the heart continues to beat throughout the ablation procedures. Commonly, the choice of placement of the catheter is determined by a combination of electrophysiological guidance and fluoroscopy (placement of the catheter in relation to known features of the heart, which are marked by radiopaque diagnostic catheters that are placed in or at known anatomical structures, such as the coronary sinus, high right atrium, and the right ventricle).

The energy necessary to ablate cardiac tissue and create a permanent lesion can be provided from a number of different sources. Originally, direct current was utilized although laser, microwave, ultrasound, and other forms of energy have also been utilized to perform ablation procedures. Thermal ablation catheters have also been used. During thermal ablation procedures, a heating element, secured to the distal end of a catheter, heats thermally conductive fluid, which fluid then contacts the human tissue to raise its temperature for a sufficient period of time to ablate the tissue.

Conventional ablation procedures utilize a single distal electrode secured to the tip of an ablation catheter. Increasingly, however, cardiac ablation procedures utilize multiple electrodes affixed to the catheter body. These ablation catheters often contain a distal tip electrode and a plurality of ring electrodes. Mapping catheters also often contain a plurality of sensing electrodes to monitor various forms of electrical activity in the human body. Sheaths may be provided for the placement and translation of an ablation or mapping catheter in a body cavity. Sheaths may also be provided with one or more electrodes for mapping of an endocardial or epicardial surface, for example.

Ablation and mapping catheters are labor-intensive to assemble. Each electrode must be individually brazed to a conductor, holes must be punctured into the catheter shaft, each conductor must be threaded through the catheter shaft, and the electrodes must be slid into their position along the catheter shaft. Some ablation and mapping catheters may have up to 20 electrodes that need to be spaced in a particular configuration. Assembling the electrodes may take up to or even more than approximately 45 minutes. Sheaths configured to include electrodes may be similarly labor-intensive to assemble.

Thus, there remains a need for improving the timing for production and ease of manufacture for an electrode assembly for a catheter or sheath, as well as increasing the reliability of the electrodes on the catheter or sheath, without sacrificing the ability of the catheter or sheath to be deflected.

BRIEF SUMMARY OF THE INVENTION

It is desirable to be able to remove the multi-conductor wiring from a catheter or sheath, since multi-conductor wiring is highly labor-intensive and results in an increased assembly time. It is also desirable to be able to indicate the desired locations of the electrodes on the catheter or sheath prior to assembly to further speed up assembly time. It may also be desirable to increase the reliability of the electrodes on the catheter or sheath by making the electrodes integral with the conductor to prevent any unreliability that may be associated with the weld between discrete electrodes and conductors. Finally, it may be desirable to modify the design of a conductor for a catheter or sheath without sacrificing the ability of the catheter or sheath to be deflected, which is necessary for the applications of each.

A circuit configured for connecting an electrode to a catheter or sheath is provided. The circuit includes a member having a longitudinal axis and configured to extend along at least a portion of the length of the catheter or sheath. The circuit further includes a trace printed on the member, where the trace includes at least a longitudinal segment extending generally along at least a portion of the longitudinal axis and a transverse segment extending generally transverse to the longitudinal axis. The circuit further includes a pad integral with and extending from the circuit proximal the transverse segment of the trace. A catheter or sheath assembly comprising the circuit and an electrode connected to the circuit are also provided. A method of forming a catheter or sheath assembly is also provided comprising the steps of providing a circuit, connecting an electrode to the circuit, and reflowing a plastic material over the assembly for maintaining placement of the circuit and the electrode in the assembly.

The foregoing and other aspects, features, details, utilities, and advantages of the present invention will be apparent from reading the following description and claims, and from reviewing the accompanying drawings.

DETAILED DESCRIPTION OF THE INVENTION

Figure 1:
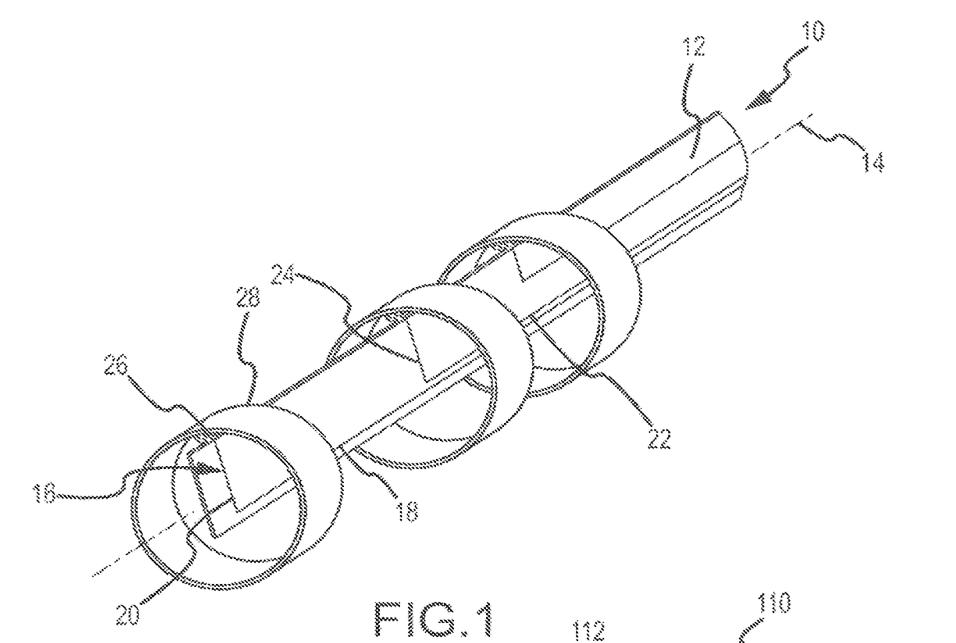
FIG. 1 is a perspective view of a circuit and electrodes for use with a catheter in accordance with a first embodiment of the invention.

A circuit configured for connecting an electrode to mapping and ablation catheters or to sheaths is provided in which no discrete wiring is required. In accordance with a first embodiment, circuit 10 may be provided for use with a mapping or ablation catheter. Referring to FIG. 1, circuit 10 may include member 12. Member 12 may have a longitudinal axis 14. Member 12 may extend along at least a portion of the length of the catheter. In some embodiments, member 12 may extend along a majority of or even substantially along the entire length of the catheter. At least a portion of member 12 may generally be flat prior to use in a catheter. A majority of member 12 or substantially all of member 12 may generally be flat prior to use in a catheter in some embodiments. At least a portion of member 12 may be generally flat when in use in a catheter. A majority of member 12 or even substantially all of member 12 may generally be flat when in use in a catheter in some embodiments. Referring again to FIG. 1, member 12 is illustrated as generally flat. Member 12 may be approximately 0.030" in width. Of course, depending upon the intended application, member 12 may have a larger or smaller width in some embodiments.

Circuit 10 may be configured to be disposed along a center of the opening of a catheter. Location of circuit 10 along the center of a catheter in the neutral axis may prevent undue stress from being placed on circuit 10 when the catheter is deflected. A neutral axis is generally defined as the axis in the cross-section of the catheter shaft along which there are no longitudinal stresses and/or strains. Some catheters may include a planarity ribbon wire extending along at least a portion of the length of the catheter in order to aid the catheter in deflection along a single axis. Circuit 10 may be configured to replace the planarity ribbon wire. In some embodiments, circuit 10 may be of increased thickness when it is configured to replace the planarity ribbon wire.

Circuit 10 may comprise a material that is flexible in order to allow for deflection of the catheter, or sheath in some embodiments. However, circuit 10 may also comprise a material that is of sufficient rigidity to maintain the electrical integrity of the circuit. Circuit 10 may comprise a polymer or plastic. For example, circuit 10 may comprise polyimide or polyethylene terephthalate polyester. In some embodiments, circuit 10 may comprise KAPTON® or MYLAR® available from E.I du Pont de Nemours and Company.

Circuit 10 includes a trace 16 included (e.g., printed) on member 12. The trace may comprise platinum or gold or copper (e.g., copper plated with platinum, gold, or silver). Trace 16 may include a longitudinal segment 18 extending generally along the longitudinal axis 14 of member 12 and a transverse segment 20 extending generally transverse to the longitudinal axis 14. The proximal end of longitudinal segment 18 of trace 16 may originate at a solder pad that is compatible with a circuit connector conventional in the art (e.g., a zif type connector). Trace 16 may be about 0.002" to about 0.003" in width. Of course, depending upon the intended application, trace 16 may have a larger or smaller width. Trace 16 may also be disposed between a first and second layer of insulation, with the trace and insulating layers being about 0.003" to about 0.008" in thickness. Again, depending upon the intended application, trace 16 and the insulating layers may be more or less thick. Member 12 may include a plurality of traces. For example, member 12 may include three traces as illustrated in FIG. 1. Member 12 may include fewer or more traces. If member 12 includes a plurality of traces, the longitudinal segment of each trace may extend a different length along longitudinal axis 14 of member 12, so that the each transverse segment is disposed at a different length along member 12. For example, longitudinal segment 22 of a second trace illustrated in FIG. 1 is a different length than longitudinal segment 18 of trace 16. Transverse segment 24 of a second trace illustrated in FIG. 1 is therefore at a different location along the length of member 12. Accordingly, a plurality of electrodes may be connected to circuit 10 proximal the transverse segment of each trace at different locations along the length of member 12. Circuit 10 may include other trace patterns (e.g., where the trace does not extend along the longitudinal axis or transverse to the longitudinal axis, but at any number of angles or directions).

Circuit 10 may include a pad 26 extending beyond the edge of member 12. Pad 26 may be integral with member 12. Pad 26 may extend from member 12 proximal the transverse segment 20 of trace 16. The transverse segment 20 may terminate into pad 26 in an embodiment. Pad 26 may extend generally transversely from longitudinal axis 14 of member 12. Pad 26 may be configured for connection to electrode 28. Pad 26 may comprise a built-up or heavy solder pad which may be formed around the catheter shaft so that it may be configured for contact with the inner surface of electrode 28. Pad 26 may generally be smaller in width than electrode 28. Pad 26 may also be of sufficient length to allow for proper positioning of electrode 28 over it.

Electrode 28 may be provided on the catheter for ablation or mapping. For example, electrode 28 may emit an electrical stimulus to create tissue necrosis and/or electrode 28 may comprise a sensing electrode to monitor various forms of electrical activity in the human body. In an embodiment, electrode 28 may comprise a ring or a band. Accordingly, electrode 28 may include both an inner surface and an outer surface. In an embodiment, electrode 28 may be approximately 7 French (e.g., about 0.030") in cross-sectional dimension. Electrode 28 may have a larger or smaller cross sectional dimension in some embodiments. The width of electrode 28 may, for example, be about 1.5 mm. Of course, depending on the intended application, electrode 28 may have a larger or smaller width. For some embodiments, electrode 28 may be comprised of platinum. Electrodes 28 may be welded to pad 26. For example, electrodes 28 may be laser welded to pad 26. Pad 26 may have about 0.005" of solder discretely positioned on it so that electrode 28 may be soldered in place once it has been positioned over pad 26. During assembly, laser energy may be focused onto the outer surface of electrode 28 to create a solder puddle which would solder itself to the inner surface of electrode 28. Electrode 28 may further be connected to circuit 10 using a conductive adhesive.

Figure 2:
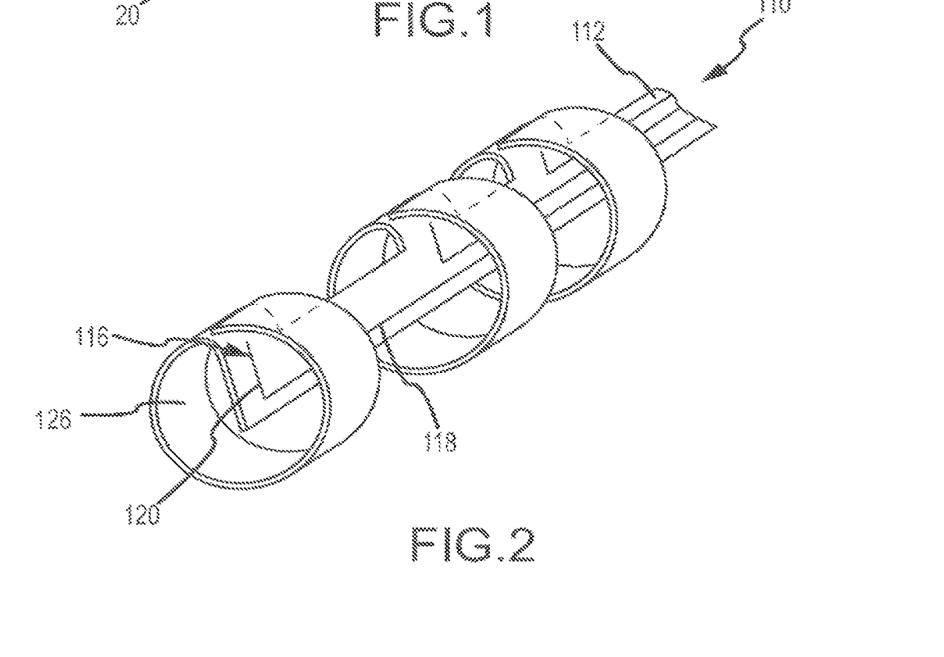
FIG. 2 is a perspective view of a circuit and electrodes for use with a catheter in accordance with a second embodiment of the invention.

Referring now to FIG. 2, a circuit 110 in accordance with a second embodiment of the invention is provided. Circuit 110 may be substantially similar to circuit 10, including member 112 and trace 116, but circuit 110 may include a ring extension or pad 126 that is comparatively wider and longer than pad 26. For example, ring extension or pad 126 may be about 1.5 mm wide and have a length about equal to the circumference of a 7 French catheter (e.g., about 0.30"). Ring extension or pad 126 may be configured to form an electrode ring or pad for ablation and/or mapping applications. Pad 126 may be biocompatible and may be of sufficient composition and/or density to facilitate visualization under fluoroscopy. Pad 126 may comprise gold or platinum and, depending upon the intended configuration, may not be masked. For example, pad 126 may comprise gold or platinum plating that is about 0.0015" to about 0.0020" thick. Pad 126 may be integral with member 112. Pad 126 may extend from member 112 proximal a transverse segment 120 of trace 116. The transverse segment 120 may terminate with or into pad 126. Pad 126 may extend generally transversely to the longitudinal axis of member 112. Further, pad 126 may be configured to be formed (e.g., rolled) into a ring to form an electrode for use in connection with the catheter. The formed pad 126 may be adhesive-backed to allow for positioning on the catheter shaft (e.g., 7 French catheter). During the reflow processing, the catheter or sheath shaft may be bonded to the circuit 110 to hold it in position. In some embodiments, circuit 110 may be fabricated with approximately one to twenty pads, each pad configured to be formed or rolled into a ring to form a portion of an electrode. If fewer electrodes were required in a catheter or sheath assembly than on the fabricated circuit, then the extra pads 126 could easily be removed (e.g. cut-off). In some embodiments, two or more circuits 110 could be utilized in tandem to achieve the desired number of pads for forming the desired number of electrodes or electrode portions.

Figure 3:
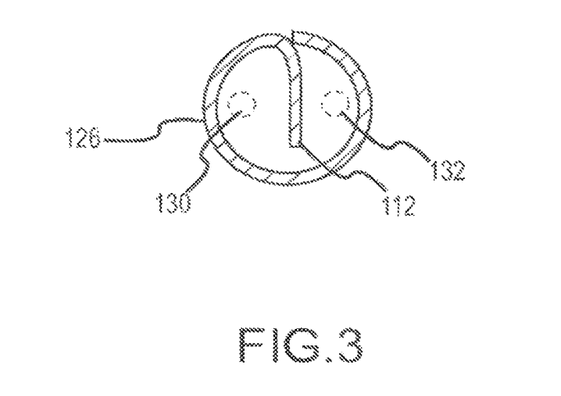
FIG. 3 is a front cross-sectional view of a circuit and electrodes for use with a catheter in accordance with the second embodiment of the invention.

Referring now to FIG. 3, circuit 110 may be disposed along the neutral axis of the catheter. Accordingly, a first pull wire 130 may be disposed on a first side of member 112, and a second pull wire 132 may be disposed on a second (e.g., diametrically opposing) side of member 112. In an embodiment as generally illustrated in FIG. 3, the first and second pull wires 130, 132 may be disposed generally alongside a centerline of member 112.

Figure 4:
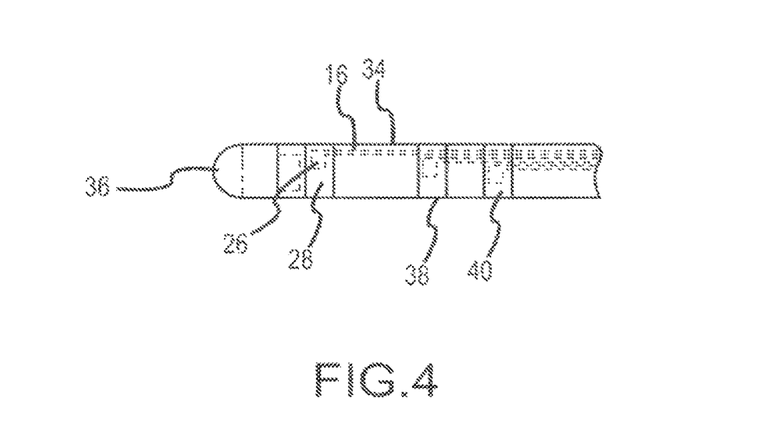
FIG. 4 is a side cross-sectional view of a circuit and electrodes embedded in a catheter in accordance with the first or second embodiment of the invention.

Referring now to FIG. 4, after each electrode is connected (i.e., whether by connector or initial formation as part of the circuit) to circuit 10 (or 110), the entire catheter shaft can be formed (e.g., reflowed with material) in order to seal and/or secure the placement of circuit 10 (or 110) and the electrodes 28 (or 126). The electrodes 28 (or 126) may be bonded and/or adhered to the shaft during the reflow process. The reflow material 34 may comprise plastic. In an embodiment, the reflow material 34 may comprise polyether block amides. In an embodiment, the reflow material 34 may comprise PEBAX®. However, during deflection of the catheter or sheath, the electrodes may loosen (i.e., the circuit 10, 110 away from the electrodes 28, 126 may be pulled and compressed, causing the circuit to move, push back, and even buckle. Placement of the circuit 10, 110 in spaghetti tubing may be utilized to allow for some movement (e.g., slight movement) of the circuit within the catheter or sheath shaft to try to prevent buckling. For example, without limitation, the spaghetti tubing may comprise polytetrafluoroethylene (PTFE) and may be disposed between the circuit 10, 110 and the material of the shaft of the catheter or sheath. For a circuit with more complicated geometry, holes may need to be provided in the spaghetti tubing to allow for protrusion of the pads or rolled electrodes. As shown in FIG. 4, the catheter may further include a tip 36 configured for tissue ablation. Referring still to the embodiment illustrated in FIG. 4, a first electrode 28 may be disposed, for example, about 2 mm away from the ablation tip 36. A second electrode 38 may be disposed, for example, about 5 mm away from the first electrode 28. A third electrode 40 may be disposed, for example, about 2 mm away from the second electrode 38. Additional electrodes may be disposed in the same pattern along the length of the catheter. The distance between the ablation tip and the electrode and/or between adjacent electrodes may be greater or less then 2 mm or 5 mm in connection with other embodiments.

Figure 5:
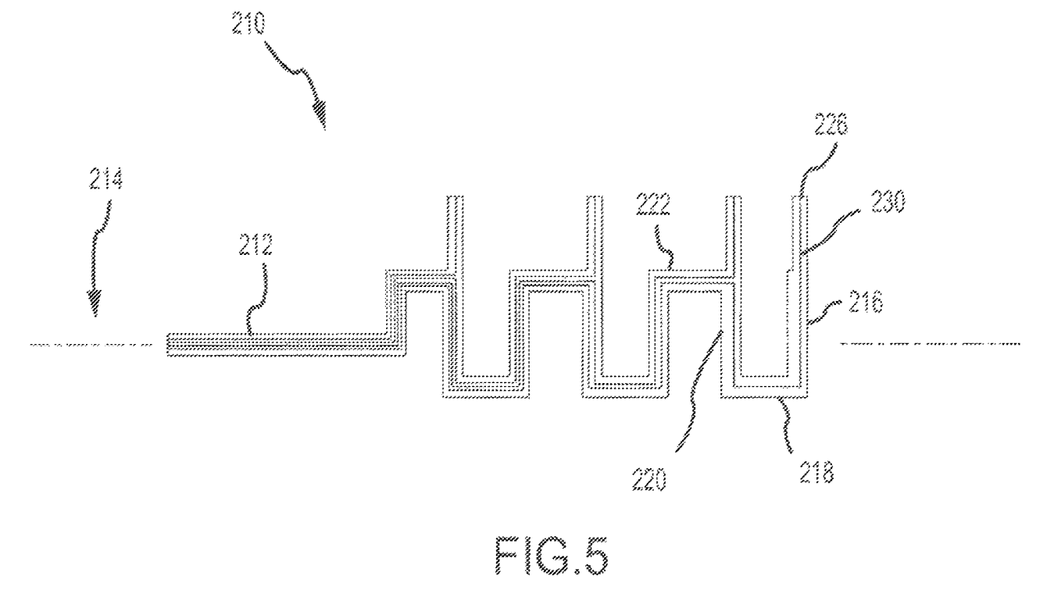
FIG. 5 is a top plan view of a circuit for use with a catheter or sheath in accordance with a third embodiment of the invention.
Figure 6:
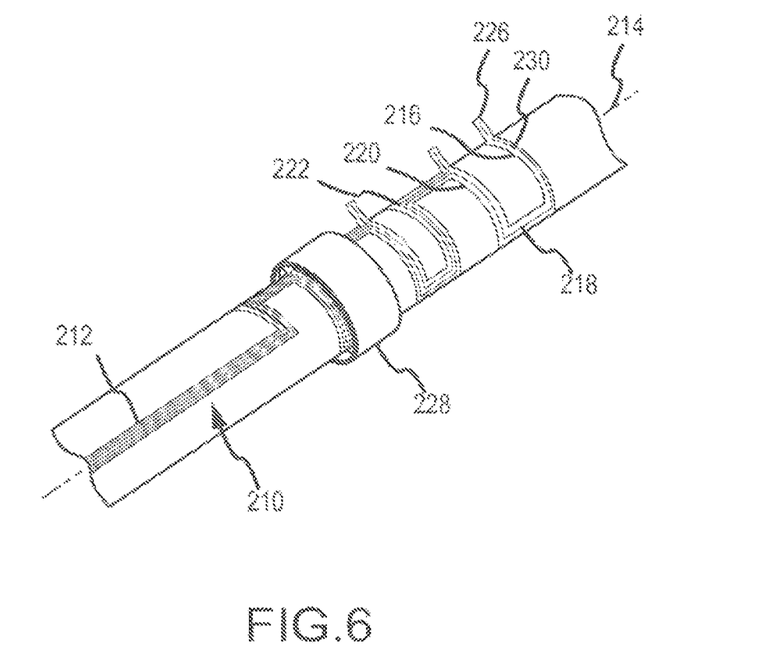
FIG. 6 is a perspective view of a circuit and electrodes for use with a catheter or sheath in accordance with a third embodiment of the invention.

In accordance with a third embodiment, circuit 210 may be provided for use in connection with a mapping or ablation catheter and/or a sheath and/or another tubular object configured for insertion into a body cavity or blood vessel. Referring now to FIGS. 5 and 6, circuit 210 may include a member 212. Member 212 may have a longitudinal axis 214. Member 212 may extend along at least a portion of the length of the catheter or sheath. In some embodiments, member 212 may extend along a majority of or even substantially the entire length of the catheter or sheath. At least a portion of member 212 may generally be flat prior to use in a catheter or sheath as shown in the embodiment generally illustrated in FIG. 5. A majority of member 212 or even substantially all of member 212 may generally be flat prior to use in a catheter or sheath in some embodiments.

Referring again to FIGS. 5 and 6, member 212 may include a first transverse segment 216 extending generally transverse to longitudinal axis 214. Member 212 may include a first longitudinal segment 218 extending generally along at least a portion of longitudinal axis 214. Member 212 may include a second transverse segment 220 extending generally transverse to longitudinal axis 214. Member 212 may include a second longitudinal segment 222 extending generally along at least a portion of longitudinal axis 214. First and second longitudinal segments 218 and 222 may be configured to be disposed on opposing sides of a catheter or sheath (e.g., approximately 180° apart). Further, at least a portion of member 212 may be curved when it is embedded within a catheter shaft or a sheath. A majority of member 212 or even substantially all of member 212 may be generally curved when it is embedded with a catheter shaft or sheath. In an embodiment, each transverse segment (e.g., 216, 220) may extend approximately one-half of the circumference of the catheter or sheath. In other embodiments, each transverse segment (e.g., 216, 220) may extend less than one-half of the circumference of the catheter or sheath or more than one-half of the circumference off the catheter or sheath. Each transverse segment (e.g., 216, 220) may be configured to be about one-half of the circumference of a 7 French size catheter or sheath. However, each transverse segment may be configured to be used with any size catheter or sheath (e.g., 6 French or 5 French size catheter or sheath). Member 212 may include a pad 226. Pad 226 may be substantially aligned with transverse segment 216 and may extend generally transversely to the longitudinal axis 214 of member 212. In the third embodiment, pad 226 may be configured for connection to an electrode 228 similar to the first embodiment illustrated in FIG. 1. In a fourth embodiment, pad 226 may be configured to be rolled or otherwise formed into an electrode similar to the configuration illustrated in FIG. 2. Member 212 may comprise a material that is flexible in order to allow for deflection of the catheter or sheath. Member 212 may also comprise a material that has sufficient rigidity to maintain the electrical integrity of the circuit. Member 212 may comprise a polymer or plastic. For example, without limitation, member 212 may comprise polyimide or polyethylene terephthalate polyester. In some embodiments, member 212 may comprise KAPTON® or MYLAR®.

Referring again to FIGS. 5 and 6, pad 226 may have a reduced profile and, depending upon the intended circumstance or application, may not be masked to provide connection to another component (e.g., an electrode). In some embodiments, electrodes 228 may be welded (e.g., laser welded) to pads 226 substantially as described in connection with circuit 10 in the first embodiment. In other embodiments, pads 226 may be substantially thicker and longer as described in connection with circuit 110 in the second embodiment such that pads 226 may be configured to be rolled or otherwise formed into an electrode.

Still referring to FIG. 5, member 212 may comprise a plurality of transverse and longitudinal segments and a plurality of pads. For example, illustrated member 212 includes six transverse segments, four of which are aligned with four pads, as illustrated in FIG. 5. Member 212 further includes six longitudinal segments as illustrated in FIG. 5. Member 212 may include fewer or more transverse and longitudinal segments. Each of the transverse segments may be disposed at a different length of member 212 so that each electrode may be disposed at a different location along the length of member 212. In an embodiment, pads 226 may be spaced, for example, approximately 10 mm apart along the length of member 212. In other embodiments, pads 226 may be spaced closer or further apart.

Member 212 may include a trace 230. Trace 230 may, for instance, comprise platinum or gold or copper (e.g., copper plated with platinum, gold, or silver). The proximal end of trace 230 may originate at a solder pad that is compatible with a circuit connector conventional in the art (e.g., a zif type connector). The trace may extend along each of the longitudinal segments and each of the transverse segments of member 212. Trace 230 may terminate with, at, or about pad 226. Additional traces may be printed on member 212 if member 212 includes additional pads to which electrodes are or may be connected. For example, four traces are illustrated in FIGS. 5-6. The proximal end of each trace may originate at a solder pad that is compatible with a circuit connector conventional in the art, and each trace may extend along the longitudinal segments and transverse segments of member 212 and terminate at a different pad disposed at a different length along longitudinal axis 214 of member 212. Accordingly, an electrode connected to each pad or formed from each pad may be disposed at a different location along the length of member 212. Member 212 may include other trace patterns (e.g., where the trace extends in any number of angles or directions).

Figure 7:
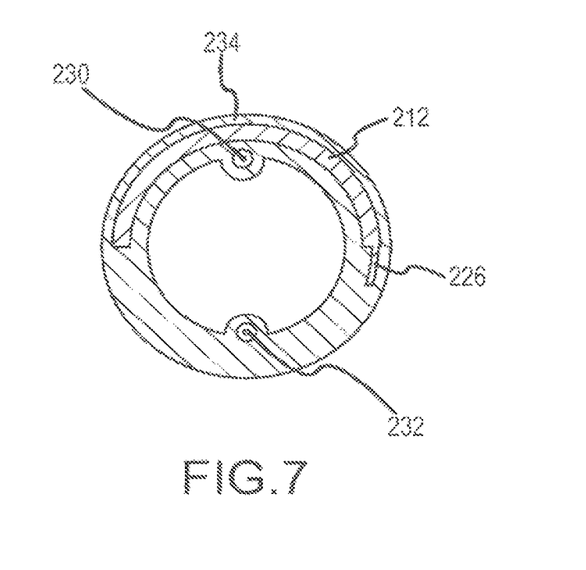
FIG. 7 is a front cross-sectional view of a circuit and electrodes for use with a catheter or sheath in accordance with a third embodiment of the invention.

Referring now to FIG. 7, member 212 may be positioned so that the longitudinal segments 218 of member 212 may be positioned on or about the neutral axis of the catheter or sheath shaft. Accordingly, a first pull wire 230 and a second pull wire 232 may be disposed approximately 90° from an end of transverse segment 216 of member 212. This geometry and the positioning at the neutral axis may permit circuit 210 to maintain electrical integrity and avoid shaft disruption.

As with the first and second embodiments, after each electrode is connected to member 212 or formed from pads 226, the entire catheter shaft can be formed (e.g. reflowed with material) in order to seal and/or secure the placement of circuit 210 and the electrodes. The electrodes may be bonded and/or adhered to the shaft during the reflow process. The reflow material 234 may comprise plastic. In an embodiment, the reflow material 234 may comprise polyether block amides. In an embodiment, the reflow material may comprise PEBAX®.

Although four embodiments of this invention have been described above with a certain degree of particularity, those skilled in the art could make numerous alterations to the disclosed embodiments without departing from the spirit or scope of this invention. All directional references (e.g., upper, lower, upward, downward, left, right, leftward, rightward, top, bottom, above, below, vertical, horizontal, clockwise, and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. An apparatus, comprising:
a shaft comprising a distal portion and a proximal portion, wherein the shaft is configured to be guided through a vasculature;
at least one electrode coupled to the distal portion of the shaft; and
a flexible circuit comprising a member and at least one conductive element traversing the shaft between the electrode and the proximal portion, wherein the member comprises a longitudinal axis and is configured to extend along a least a portion of the length of the shaft, wherein the at least one conductive element is disposed on the member, wherein the flexible circuit extends through a neutral axis of the shaft about which the shaft is configured to deflect, and wherein the flexible circuit is configured to aid in the deflection of the shaft.

2. The apparatus of claim 1, wherein the flexible circuit-further comprises a pad disposed at a distal end of the flexible circuit-and wherein the pad is configured to electrically couple to the at least one electrode.

3. The apparatus of claim 2, wherein the flexible circuit comprises a first flexible circuit and the apparatus further comprises a second flexible circuit comprising a second pad configured to be coupled to a second electrode.

4. The apparatus of claim 1, wherein the shaft further comprises at least one pull wire extending along the shaft, wherein the at least one pull wire is substantially orthogonal to a longitudinal axis of the flexible circuit.

5. The apparatus of claim 4, wherein the shaft further comprises a first pull wire and a second pull wire and wherein the first pull wire and the second pull wire extend along the shaft and are located on opposite sides of the flexible circuit and are located substantially orthogonal to the longitudinal axis of the flexible circuit.

6. The apparatus of claim 1, wherein the flexible circuit further comprises a trace.

7. The apparatus of claim 1, wherein the shaft is configured to deflect in a first direction.

8. The apparatus of claim 7, wherein the shaft further comprises at least one pull wire extending along the shaft, wherein the at least one pull wire is substantially orthogonal to a longitudinal axis of the flexible member.

9. The apparatus of claim 1, further comprising at least one pull wire extending along the shaft, wherein the at least one pull wire is substantially orthogonal a longitudinal axis of the shaft.

10. The apparatus of claim 2, wherein the at least one electrode comprises at least one ring electrode and wherein each of the ring electrodes encircles a respective portion of a circumference of the shaft.

11. The apparatus of claim 10, wherein the at least one electrode comprises a plurality of electrodes.

12. The apparatus of claim 10, wherein the ring electrode is integral with the pad.

13. An apparatus, comprising:
a shaft comprising a distal portion and a proximal portion, wherein the shaft is configured to be guided through a vasculature;
at least one electrode coupled to the distal portion of the shaft; and
a flexible circuit comprising a member, a pad, and at least one conductive element, wherein the member comprises a longitudinal axis and is configured to extend along a least a portion of the length of the shaft, wherein the at least one conductive element is disposed on the member, wherein the conductive element comprises a longitudinal segment, and a transverse segment, wherein the longitudinal segment, the transverse segment and the pad are electrically coupled, wherein the flexible circuit extends to the proximal portion of the shaft, and wherein the pad is electrically coupled to the at least one electrode, and wherein the flexible circuit extends through a neutral axis of the shaft about which the shaft is configured to deflect.

14. The apparatus of claim 13, wherein the flexible circuit further comprises a trace.

15. The apparatus of claim 13, wherein the shaft is configured to deflect in a first direction.

16. The apparatus of claim 15, wherein the shaft further comprises at least one pull wire extending along the shaft, wherein the at least one pull wire is substantially orthogonal to a longitudinal axis of the flexible member.

17. The apparatus of claim 13, wherein the at least one electrode comprises at least one ring electrode and wherein each of the at least one ring electrodes encircles a respective portion of a circumference of the shaft.

18. An apparatus, comprising:
a shaft comprising a distal portion and a proximal portion, wherein the shaft is configured to be guided through a vasculature;
a first electrode coupled to the distal portion of the shaft;
a second electrode coupled to the distal portion of the shaft;
a member comprising a longitudinal axis, a first flexible circuit, and a second flexible circuit, wherein the member is configured to extend along a least a portion of the length of the shaft, wherein the first flexible circuit and the second flexible circuit are disposed on the member, and wherein the flexible circuit extends through a neutral axis of the shaft about which the shaft is configured to deflect,
the first flexible circuit comprising a first longitudinal segment, a first transverse segment, and a first pad, wherein the first longitudinal segment, the first transverse segment and the first pad are electrically coupled, wherein the first flexible circuit extends to the proximal portion of the shaft, and wherein the first pad is electrically coupled to the first electrode; and
the second flexible circuit comprising a second longitudinal segment, a second transverse segment, and a second pad, wherein the second longitudinal segment, the second transverse segment and the second pad are electrically coupled, wherein the second flexible circuit extends to the proximal portion of the shaft, and wherein the second pad is electrically coupled to the second electrode.

* * * * *